US00PP14324P29

(12) United States Plant Patent
Hanes

(10) Patent No.: US PP14,324 P2
(45) Date of Patent: Nov. 25, 2003

(54) PETUNIA PLANT NAMED REFLEC WHITE

(50) Latin Name: *Petunia hybrida*
Varietal Denomination: Reflec White

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/403,318
(22) Filed: Mar. 31, 2003
(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates, PC

(57) ABSTRACT

A petunia cultivar particularly distinguished by white colored flowers, compact habit and good basal branching.

1 Drawing Sheet

Genus and species: Petunia hybrida.
Variety denomination: 'Reflec White'.

BACKGROUND OF THE NEW PLANT

The present invention comprises a new and distinct cultivar of petunia, botanically known as Petunia hybrida, and hereinafter referred to by the cultivar name 'Reflec White'. The new cultivar is asexually reproduced from vegetative cuttings and tissue culture resulting from the cross of the seed/pod parent 99-207-3, a pink trailing proprietary line that is unnamed and unpatented ×99-161-1, a double pink proprietary line that is unnamed and unpatented.

'Reflec White' is a product of a planned breeding program intended to create new petunia plants with white colored flowers, compact habit, good basal branching and moderately vigorous growth.

The new cultivar was created in 1999 in Gilroy, Calif. and has been asexually reproduced repeatedly by vegetative cuttings and tissue culture in Gilroy, Calif., Andijk, The Netherlands, and Guatemala over a three-year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The Photograph shows the mature flowers.

DESCRIPTION OF THE NEW CULTIVAR

The following detailed descriptions set forth the distinctive characteristics of 'Reflec White'. The data, which defines these characteristics, were collected from asexual reproductions carried out in Gilroy, Calif. The plant history was taken on 6 months old plants grown in one-gallon pots in fall/winter season, in a poly-covered greenhouse under 2–4 hours supplemental light and color readings were taken in the greenhouse in the winter season under natural light. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright and decumbent.
Growth and branching habit: Good vigorous habit, well-branched, full plant.
Height: From soil level to top of blooms: Approximately 15–25 cm.
Width: Approximately 60–70 cm including flowers.
Time to produce a finished flowering plant: 8–11 weeks.
Outdoor plant performance: Full sun, free-flowering through the summer, some heat tolerance. Use as a hanging plant, in mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 6.2–6.6 cm.
Width: 3.5–3.9 cm.
Leaf blade shape: Elliptic.
Leaf margin: Entire.
Apex aspect: Acute.
Base aspect: Acuminate.
Leaf color: Upper side, close to RHS 137A (green); Underside, close to RHS 147C (yellow-green).
Texture: Occasional glandular hairs.
Venation: Palmate.
Venation color: RHS 144B (yellow-green).
Petiole length: 0.7–1.0 cm.
Petiole width: 0.3 cm.
Petiole color: RHS 144B (yellow-green).
Petiole texture: Long glandular hairs.

THE STEM

Length: 40–50 cm.
Diameter: 0.35–0.4 cm.

Internode length: 3.0–5.0 cm.
Color: RHS 145B (yellow-green).
Texture: Much long glandular hair.
Stem anthocyanin: No.
Peduncle color: Between RHS 144A and B (yellow-green).
Peduncle length: 6.0–6.3 cm.
Peduncle diameter: 0.2 cm.
Peduncle texture: Many glandular hairs.

THE BUD

Shape: Orbicular.
Diameter: 0.7–1.0 cm.
Length: 1.3–1.7 cm.
Color at tight bud: RHS 150C (yellow-green) base color with RHS 144C (yellow-green) mid-veins.

THE FLOWER

Blooming habit: Continuous all through the growing season. Good floriferousness.
Inflorescence type: Flowers solitary in upper leaf axis.
Young flower color: White base color, more white than RHS N155D, with RHS# 144C (yellow-green) mid-veins and RHS 144C and D (yellow-green) secondary veins.
Mature flower color: Front side, white base color, more white than RHS N155D, with RHS 144C (yellow-green) mid-veins and faint RHS 144C and D (yellow-green) secondary veins; Underside, white base color, more white than RHS N155D, with RHS 144C (yellow-green) mid-veins and faint RHS 145D (yellow-green) secondary veins.
Corolla tube color inside: White base color, more white than RHS N155D, with RHS N144D (yellow-green) mid-veins and RHS 144D (yellow-green) secondary veins.
Corolla tube length: 2.5 cm to petal flare.
Corolla outside texture: Many glandular hairs.
Floret type: Funnel form, fully double flowers approximately 10 lobes and outer petals fused at base and inner petals not fused at base.
Flower (limb) diameter: 5.0–6.0 cm.
Petal apex shape: Acute.
Petal margin: Entire.
Petal waviness of petal: Moderate.
Petal lobation: Moderate.
Petal texture: Papillose.
Calyx: 5 deeply lobed.
Sepal color: RHS 137B (green).
Sepal length: 2.3–2.4 cm.
Sepal width: 0.6–0.7 cm.
Sepal shape: Oblong to Elliptic.
Sepal apex: Rounded.
Sepal texture: Many glandular hairs.
Lastingness of individual blooms: 4–8 days.
Fragrance: None.

THE REPRODUCTIVE ORGANS

Stamens: 10–20.
Filament color: White.
Pollen color: RHS 158A (yellow-white).
Pistil: One, when present. Plants are heterozygous and do not always produce a pistil.

DISEASE AND INSECT RESISTANCE

Not observed.

COMPARISON WITH KNOWN CULTIVARS

'Reflec White' differs from the female parent 99-207-3 in the following ways: The female parent has pink flowers that are single in flower form. 'Reflec White' has white flowers that are double in flower form and a more vigorous plant.

'Reflec White' differs from the male parent 99-161-1 in the following ways: The male parent has pink flowers that are double in flower form on a plant that grows more upright. 'Reflec White' has white double flowers on a plant that is less upright and more spreading in growth.

I claim:

1. A new and distinct petunia plant as shown and described herein.

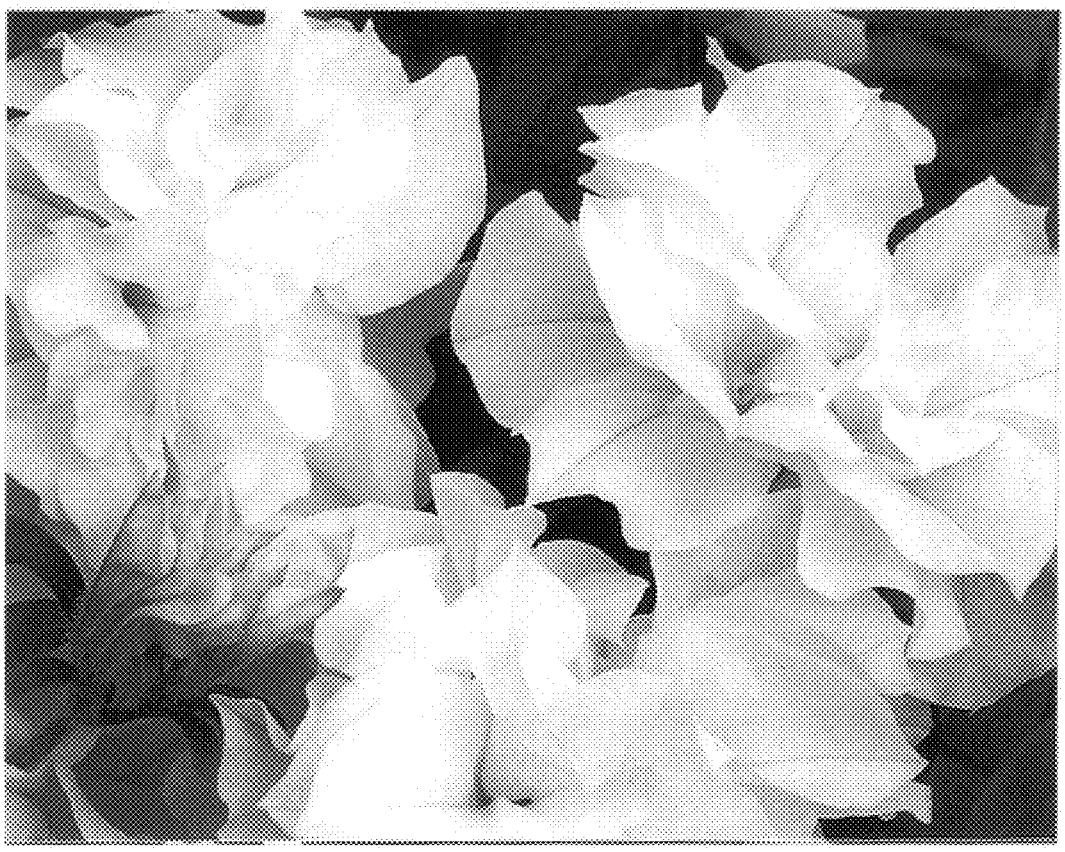

* * * * *